United States Patent [19]

Brown

[11] Patent Number: 5,817,619
[45] Date of Patent: Oct. 6, 1998

[54] **PROTEIN FROM *ALBUS ALBOPICTUS* CELLS AND METHOD FOR ITS USE**

[75] Inventor: Dennis T. Brown, Austin, Tex.

[73] Assignee: Research Development Foundation, Carson City, Nev.

[21] Appl. No.: 558,347

[22] Filed: Nov. 16, 1995

Related U.S. Application Data

[63] Continuation of Ser. No. 186,806, Jan. 25, 1994, abandoned.

[51] Int. Cl.⁶ .............................. A01N 37/48; C07K 1/00
[52] U.S. Cl. .............................. 514/2; 435/70.3; 530/350
[58] Field of Search .......................... 530/350; 435/70.3; 514/2

[56] References Cited

U.S. PATENT DOCUMENTS 4,859,464  8/1989  D'Antonio ................................ 424/88
5,217,879  6/1993  Huang et al. .......................... 435/69.1

OTHER PUBLICATIONS

Miller et al (1993) Journal of General Virology, 74, 293–98.

Luo et al (1993) Virology, 194, 44–49.

*Primary Examiner*—Irene Marx
*Attorney, Agent, or Firm*—Benjamin Aaron Adler

[57] ABSTRACT

The present invention provides a novel isolated and purified protein that is produced by *Aedes albopictus* L4.4 cells, having a molecular weight of 55 kDa of SDS-PAGE, is associated with lysosomal membranes and induces an anti-viral state. This anti-viral state is characterized by a total block of virus RNA synthesis with no effect of cell macromolecular synthesis. Also provided are various methods of using this novel protein or the gene encoding this protein.

3 Claims, 4 Drawing Sheets

PROTEIN FROM *ALBUS ALBOPICTUS* CELLS AND METHOD FOR ITS USE

This is a continuation of application Ser. No. 08/186,806, filed on Jan. 25, 1994, now abandoned.

BACKGROUND OF THE INVENTION

1. Field of the Invention

The present invention relates generally to the fields of virology and protein chemistry. More specifically, the present invention relates to a novel 55 kDa membrane protein associated with lysosomes.

2. Description of the Related Art

Alphaviruses are membrane-containing plus polarity RNA viruses which are sustained in nature by a life cycle which includes vertebrates. Sindbis virus is the prototype of the alphaviruses. Alphavirus infection of tissue cultured mosquito cells results in an acute infection (accompanied by the production of a high concentration of virus) which is followed by a persistent phase of infection in which virus production occurs at a much slower rate. These persistently infected cells may be cultured indefinitely.

Alphaviruses are propagated in nature in both vertebrate and invertebrate hosts. Cultured cells of vertebrate and invertebrate origin are susceptible to infection by Sindbis virus, the prototype of the alphaviruses. Although tissue cultured cells differ in their ability to produce alphaviruses, most cell lines replicate alphavirus genomes and produce viral RNA.

Comparative studies of Sindbis virus replication in cultured vertebrate and invertebrate cells have revealed differences in the morphological and biochemical aspects of virus growth, as well as in the response of the host cells to virus infection.

The most striking difference in comparative studies on the growth of alphaviruses in cultured vertebrate and invertebrate cells is the cellular response to virus infection. When cultured vertebrate cells are infected with an alphavirus, synthesis of host protein and RNA is rapidly terminated. High yields of progeny virions are accompanied by gross cytopathic effects, cell death, and lysis 10 to 20 hours post-infection. In contrast, after an initial acute phase of infection (during which yields of virus equivalent to those produced by vertebrate cells are realized), cultured mosquito cells survive infection by alphaviruses to produce persistent infections. Persistently infected mosquito cells produce virus at a much slower rate and may be cultured indefinitely.

Cultures of the U4.4 subclone of *A. albopictus* (mosquito) cells persistently infected with Sindbis virus produce a low molecular weight protein which, when applied to uninfected mosquito cells, results in the induction of an antiviral state. A similar activity has been identified in Semliki Forest virus-infected mosquito cells.

Using crude preparations of the Sindbis antiviral agent, the antiviral state was completely established after treatment of the cell for 48 hours and resulted in the inhibition of both 49S and 26S viral RNA synthesis when cells are subsequently infected with Sindbis. This Sindbis antiviral agent appears to be responsible for the low levels of virus production seen in persistently infected mosquito cell cultures. This antiviral protein (AVP) has been purified to homogeneity and is a very hydrophobic peptide of 3200 Da. Treatment of uninfected mosquito cells with this pure protein resulted in a temporary arrest of cell growth followed by return to normal growth patterns. Subsequently, the cells become refractory to infection with Sindbis virus and constitutively produce the antiviral peptide in the absence of virus or viral RNA. These unique virus-resistant mosquito cells (L4.4) have been passaged for 1.5 years without losing the virus-resistant phenotype.

The prior art is deficient in the lack of effective means of inhibiting the spread of certain viruses, including alphaviruses. The present invention fulfills this longstanding need and desire in the art.

SUMMARY OF THE INVENTION

In one embodiment of the present invention, there is provided a composition of matter comprising an isolated and purified protein that is produced by *Aedes albopictus* L4.4 cells, having a molecular weight of 55 kDa of sodium dodecyl sulfate-polyacrylamide electrophoresis (SDS-PAGE), is associated with lysosomal membranes and is produces an anti-viral state.

In another embodiment of the present invention, there is provided a pharmaceutical composition, comprising a composition of matter comprising an isolated and purified protein produced by *Aedes albopictus* L4.4 cells, having a molecular weight of 55 kDa of sodium dodecyl sulfate-polyacrylamide electrophoresis, and a pharmaceutically acceptable carrier.

In yet another embodiment of the present invention, there is provided a method of preparing the protein of claim 1, comprising the steps of: growing *Aedes albopictus* (L4.4) cells in a media; harvesting the cells; and isolating and purifying a protein secreted by *Aedes albopictus* L4.4 cells, having a molecular weight of 55 kDa of sodium dodecyl sulfate-polyacrylamide electrophoresis (SDS-PAGE) associated with lysosomal membranes from the media.

In still yet another embodiment of the present invention, there is provided a method of inhibiting the transmission of alphaviruses comprising the step of administering to a host infected infected with an alphavirus a pharmacologically effective dose of the composition of claim 2.

In another embodiment of the present invention, there is provided a method of inhibiting viral RNA synthesis comprising the step of administering to a host infected with a virus a pharmacologically effective dose of the composition of claim 2.

In yet another embodiment of the present invention, there is provided a transgenic mosquito formed by transfecting a mosquito with the gene coding for the protein of claim 1.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A shows the U4.4 cell light membrane fraction. FIG. 1B shows the L4.4 cell light membrane fraction. FIG. 1C shows the U4.4 cytosol. FIG. 1D shows the L4.4 cytosol. FIG. 1E shows the U4.4 cell P15 fraction and FIG. 1F shows the L4.4 cell P15 fraction. Equal counts were loaded on each gel and electrophoresis was carried out in two dimensions; the first dimension was run from right to left and the second dimension was run from top to bottom. Arrow heads show the positions of P55.

FIG. 2A shows the P15 fraction of non-treated U4.4 cells. FIG. 2B shows the P15 fraction of U4.4 cells after 24 hour treatment with AVP. FIG. 2C shows the P15 fraction of U4.4 cells after 48 hour treatment with AVP. FIG. 2D shows the P15 fraction from L4.4 cells as positive control. Cells were treated with AVP in [$^{35}$S] methionine/cysteine-containing medium (20 uCi/ml) for 24 or 48 hours prior to processing. Equal counts were loaded on each gel. Arrow heads show the positions of P55.

FIG. 4A shows the U4.4 mitochondrial fraction. FIG. 4B shows the L4.4 mitochondrial fraction. FIG. 4C shows the U4.4 lysosomal fraction; and FIG. 4D shows the L4.4 lysosomal fraction. Equal cpm were loaded on each gel. Arrows show the positions of P55.

DETAILED DESCRIPTION OF THE INVENTION

Figure 1:
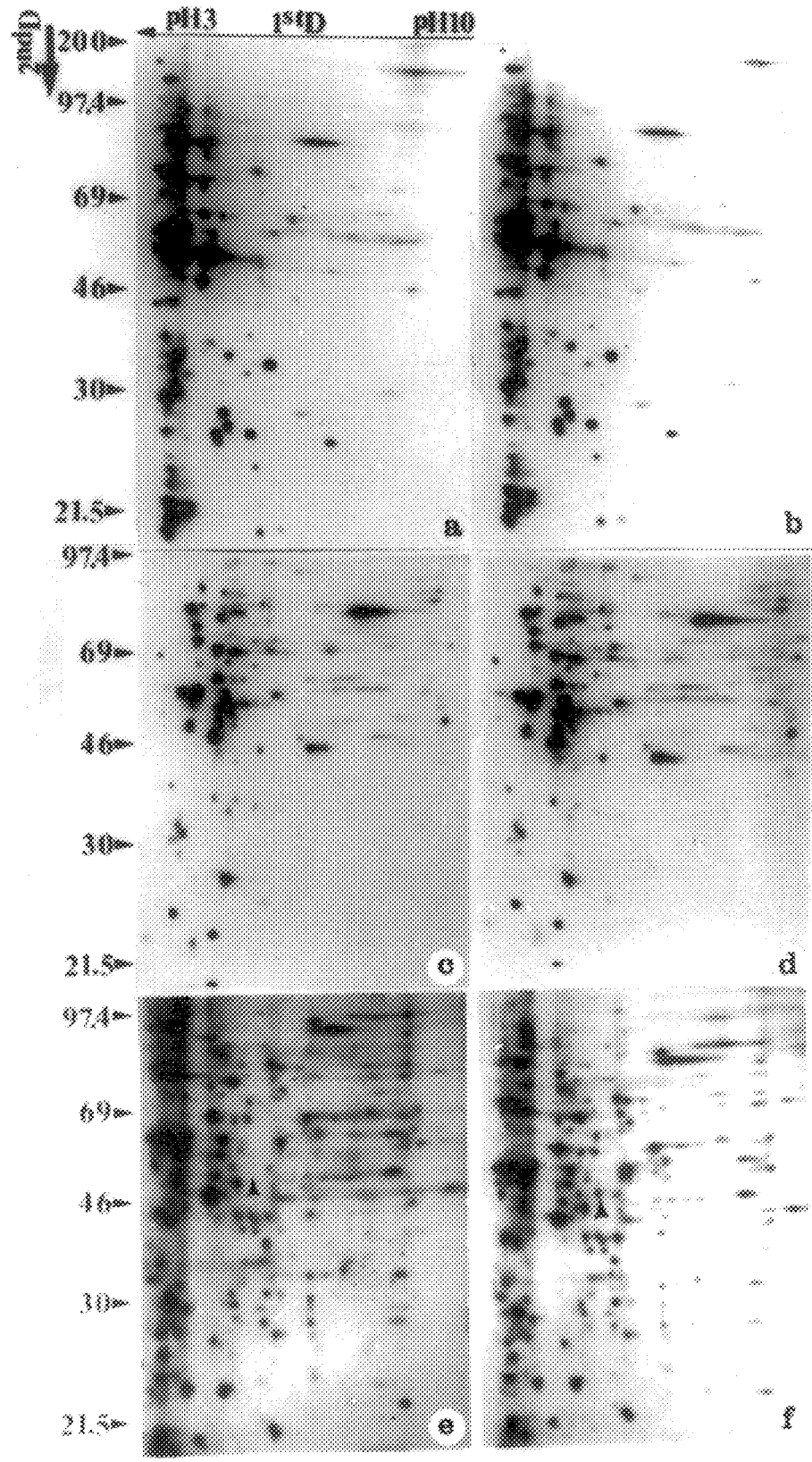
FIG. 1 shows the comparison of [$^{35}$S] methionine/cysteine labeled total cellular proteins from U4.4 and L4.4 cells. Equal numbers of cells were labeled with $^{35}$S methionine/cysteine (20 uCi/ml) for 48 hours, harvested and processed.

In the present invention, a 55 kDa lysosome-associated protein (P55) is described that is synthesized in L4.4 cells and is absent in U4.4 cells (the parent of the L4.4 cell line). There is a temporal relationship between establishment of the virus-resistant state and P55 synthesis.

The present invention is directed to a composition of matter comprising an isolated and purified protein that is produced by *Aedes albopictus* L4.4 cells, having a molecular weight of 55 kDa of SDS-PAGE, is associated with lysosomal membranes and produces an anti-viral state.

It is specifically contemplated that pharmaceutical compositions may be prepared using the novel protein of the present invention. In such a case, the pharmaceutical composition comprises the novel protein of the present invention and a pharmaceutically acceptable carrier. A person having ordinary skill in this art would readily be able to determine, without undue experimentation, the appropriate dosages and routes of administration of the novel protein of the present invention.

The level of ordinary skill of the average scientist in the area of molecular virology has increased substantially in recent years. A person having ordinary skill in this art would readily be able to sequence, without undue experimentation, the P55 protein. With the knowledge of the P55 protein, a person of ordinary skill would readily clone the gene encoding the P55 protein. This gene encoding the P55 protein would then be inserted into an appropriate expression vector and mosquitos would then be transfected with this vector. These transgenic mosquitos would then be incapable of transmitting the alpha viruses.

The present invention is also directed to a method of preparing the protein of the present invention, comprising the steps of: growing *Aedes albopictus* (L4.4) cells in a media; harvesting the cells; and isolating and purifying the protein of the present invention from the membranes of the L4.4 cells. Applicant has deposited the L4.4. cell with the ATCC on Aug. 9, 1994 as accession number CRL 11699. Applicant has deposited the L4.4 cell line under the terms of the Budapest Treaty and states that the L4.4 cell line will be irrevocably and without restriction or condition released to the public upon the issuance of a patent. The U4.4 insect cell line is available from the ATCC.

The following examples are given for the purpose of illustrating various embodiments of the invention and are not meant to limit the present invention in any fashion.

EXAMPLE 1
Preparation of L4.4 and U4.4 cells

Two *A. albopictus* (mosquito) cell lines were used. U4.4 cells were cloned and have been passaged in culture for 13 years. The L4.4 cell line was established and has been passaged in culture for 1.5 years. The U4.4 clone of Aedes albopictus cells was prepared from a culture of mixed larval cells provided by the Yale Arbovirus Research Unit. The cells were cloned by limiting dilution in micro titre plates such that each well contained only one cell. The clone designated U4.4 was selected as the one clone showing best growth properties.

EXAMPLE 2
Purification of the Antiviral Protein

The L4.4 cells were produced by treating U4.4 cells with purified antiviral protein. The antiviral protein was purified from the medium of Sindbis virus-infected U4.4 cells. Two hundred milliliters of this medium was diluted with an equal volume of 0.01M phosphate-buffered saline (PBS) at 4° for 72 hours using dialysis tubing with a 12 kDa molecular weight limit. The dialysate was tested for virus contamination by plaque assay and for antiviral activity by the assay described by Riedel and Brown, *J. Viroloay*, 29, 51–60 (1979). The dialysate was concentrated by freeze drying. The antiviral protein was purified serially by high performance liquid chromatography. The crude sample of AVP was passed through a Waters column (7.8×300 mm protein pak 60 [6,8-dihydroxy-4-oxaheptylsilyl-bonded amorphous silica]). The mobile phase was 16% 100 mM Tris-HCl, 4% 100 mM Tris base, 15% 1M NaCl, 65% $H_2O$; conditions were 22°, 1.0 ml/minute flow rate at 1000 PSI and 0.30 absorption unit full scale (AUFS). The peak activity was further purified by ion exchange chromatography using a 10×100-mm protein pak (DEAE 8 hr AP1, Waters) column. The mobile phase was 0.1M PBS (eluent A) and 1M NaCl in 1M PBS (eluent B) with a gradient of 0–100% B in 60 minutes, temperature of 22 degrees, 1.0 ml/minute flow rate at 1200 PSI, 0.1 AUFS. The peak containing the antiviral activity was finally purified by reverse phase HPLC on a 2.1×250 mm C18 (Vydac) column. The mobile phase was 0.1% TFA in water (eluent A) and acetonitrile (eluent B) with a gradient of 0–60% B in 40 minutes, temperature of 22 degrees, 0.25 ml/minute flow rate at 1200 PSI, 0.05 AUFS. The peak containing the biological activity represented an average yield of 15 micrograms of peptide. This fraction produced a single band when run on a 16.5% tricine gel as described by Schagger and Jagow, *Anal. Biochem.*, 166:368–379, 1987. This purified antiviral protein was used to treat U4.4 cells to produce L4.4 cells.

EXAMPLE 3
Culturing of the U4.4 and L4.4 cells

Both cell lines were cultured in the medium of Mitsuhashi and Maramorosch, as follows (in grams per 5 liters): (1) $CaCl_2 \times 2H_2O$, 1.0; (2) KCl, 1.0; (3) $MgCl_2 \times 6H_2O$, 0.5; (4) NaCl, 35.0; (5) $NaHCO_3$ (mixed individually in water and then added), 0.6; (6) $NaH_2PO_4 \times H_2O$, 1.0; (7) yeastolate, 25.0; (8) alpha-D-glucose, 20.0; (9) lactalbumin hydrolysate, 32.5; (10) phenol red (optional), 0.05. All ingredients were combined and stirred overnight at 4 degrees. After filter sterilization, the medium was stored at 4 degrees. The pH of the medium was adjusted in each bottle to 7.2 with sterile 7.5% sodium bicarbonate immediately before use. Then 20% FCS was added. The cells were cultured by passage in the media of Mitsuhashi and Masoamorosch at dilution of 1:10. The growth was at 28° C.

EXAMPLE 4
Treatment of mosquito cells with AVP

Treatment of mosquito cells with AVP was as follows: AVP was diluted into 9 ml of the fresh mosquito cell culture medium. This medium was then used to treat uninfected U4.4 cell monolayers at 28° C. for 48 hours. The cells were then challenged with a multiplicity of infection of 100 PFU Sindbis virus. After one hour incubation, the cells were washed three times with medium to remove unabsorbed virus. The infected cells were incubated for 48 hours in fresh medium. The virus produced by these cells was titrated by plaque assay on BHK cell monolayers as described by Renz and Brown, 1978.

In studies examining induction of P55, cellular protein radiolabeling times were equalized while varying AVP treatment times either by radiolabeling for 24 hours before AVP was added to cell culture medium and continuing incubation for 24 hours (24 hour treatment). Alternatively, the radiolabel and AVP was added to cells at the same time, continuing incubation for 48 hours.

EXAMPLE 5
Fractionation of mosquito cell homogenates

Cultured mosquito cells were harvested, washed with ice-cold 10 mM PBS and incubated in ice-cold swelling buffer (10 mM HEPES, 15 mM KCl, pH 7.2) for 5 minutes. The swollen cells were centrifuged and homogenized in ice-cold breaking buffer (50 mM HEPES, 90 mM KOAc, 5 mM $MgCl_2$ and 10 mM PMSF, pH 7.2) with 32 strokes in a type A dounce homogenizer. Cell nuclei were separated by centrifugation for 10 minutes at 1000×g. The postnuclear supernatant was centrifuged at 15,000×g for 10 minutes and the pellet (P15 fraction) was resuspended in 1 ml of gradient solution (5 mM Tris-HCl, pH 7.6, 1 mm EDTA). The supernatant recovered from the P15 fraction was centrifuged for 2 hours at 100,000×g. The pellet from this centrifugation was designated the light membrane fraction and the supernatant was designated the soluble portion of the cytoplasm. The P15 fraction was further fractionated for 1 hour, 50 minutes on a 20–40% (w/v) Accudenz (Nycodenz) gradient at 52,000×g.

EXAMPLE 6
Enzyme assays

The following enzyme markers were used: beta-galactosidase (lysosomes), succinate p-iodonitrotetrazolium violet (INT) reductase (mitochondria), catalase (peroxisomes), and 5'-nucleotidase (plasma membranes). All the assays were carried out in 1.5 ml tubes. 0.1 ml samples containing the same protein concentration were used for each experiment.

Briefly, for beta-galactosidase the assay mixture contained 0.4 ml of 6 mM p-nitrophenyl beta-D-galactopyranoside, 0.5% Triton X-100, and 0.05M citrate phosphate buffer, pH 4.3. After incubation at 37° C. for 30 minutes, the reaction was terminated by the addition of 1 ml 0.25M glycine-NaOH, pH 10. Sedimentable material was removed at 15,000 rpm for 1 minute and the absorbance of the supernatant was measured at 400 nm.

Succinate INT reductase was measured by incubation at 37° C. for 10 minutes in 0.3 ml 0.01M succinate in 0.05M phosphate buffer, pH 7.5. After a second 10 minute incubation following addition of 0.1 ml INT (2.5 mg/ml in the same buffer), the reaction was stopped by adding 1 ml ethyl acetate:ethanol:TCA (5:5:1) and the absorbance was measured at 490 nm.

Catalase was assayed by incubating the sample in 0.5 ml 6 mM $H_2O_2$ in 0.01M phosphate buffer, pH 7.0, for 5 minutes at 0° C. Unreacted substrate was reacted with 0.01N $KMnO_4$ (0.7 ml) after stopping the reaction with 0.1 ml 3M $H_2SO_4$; the absorbance was measured at 480 nm. 5'-Nucleotidase was measured in a total volume of 0.5 ml containing 2 mM [8-$^{14}$C]AMP, 0.4 mM $MgCl_2$, 10 mM Tris-HCl, pH 8.0. After incubation at 37° C. for 30 minutes, the reaction was stopped by the addition of 0.3 ml 0.3N $ZnSO_4$ and 0.3 ml 0.3N $Ba(OH)_2$. The mixture was incubated at 0° C. (with occasional agitation) for 15 minutes and the precipitate was removed by centrifugation at 0° C. for 2 minutes; 0.2 ml of the supernatant was removed for counting.

EXAMPLE 7
Two dimensional gel electrophoresis

The membrane associated proteins and the concentrated soluble proteins from different cellular fractions were solubilized in sample buffer (9.5M urea, 5% 2-mercaptoethanol, 2% nonidet P-40, 1.6% ampholine pH 5–8 [Preblended], and 0.4% ampholine pH 3–10). The first dimensional electrofocusing gel was made according to O'Farrell's method (O'Farrell, P. H. (1975), High resolution two-dimensional electrophoresis of proteins, *J. Biol. Chem.* 250, 4007–4021) and (O'Farrell, P. Z. et al., (1977). High-resolution two-dimensional electrophoresis of basic as well as acidic proteins, *Cell* 12, 1133–1142 as described by Hames, B. D., and Rickwood, D. (ed) (1990), Isoelectric focusing and two-dimensional gel electrophoresis. In Gel electrophoresis of proteins, p.149–270. Oxford University Press, New York with minor modifications. Briefly, each 10.5 ml of the gel mixture contained: 5.5 grams of urea, 1.34 ml 28.38% acrylamide, 1.62% bisacrylamide, 2 ml 10% nonidet P-40, 0.4 ml 40% ampholine pH5-8, 0.1 ml 40% ampholine pH7-9, 0.1 ml 40% ampholine pH 3-10, 2 ml $H_2O$, 5 ul TEMED and 10.5 ul ammonium persulphate.

The first dimensional electrofocusing gel was run in Hoefer tube gels for 4 hours at 500 volts after prefocusing for 1 hour at 250 volts. The electrolyte solutions were 10 mM $H_3PO_4$ (anolyte) and 20 mM NaOH (catholyte). Electrofocused gels were then soaked in equilibration buffer (2.5% SDS, 5 mM DTT, 125 mM Tris-HCl pH 6.8, 10% glycerol and 0.05% bromophenol blue) for 10 minutes. Equilibrated gels were placed on 10.8% SDS-PAGE slab gels and sealed with agarose (0.2% in 0.125M Tris-HCl pH 6.8, brought to 2% SDS after cooling to 45° C.). Second dimensional electrophoresis was carried out for 5 hours at a constant power of 5 watts. Fluorography was performed and gels were exposed to Kodak XAR-5 film.

EXAMPLE 8
The L4.4 Cell Line

The L4.4 cell line was incapable of replicating Sindbis virus RNA after infection with intact virions or transfection with genomic viral RNA. L4.4 cells were found to replicate a rhabdovirus (Vesicular Stomatitis Virus) as efficiently as the U4.4 (alphavirus-sensitive) cell line. Acquisition of the virus-resistant state was accompanied by the appearance of particular cellular proteins.

EXAMPLE 9
Radiolabeled cellular proteins from U4.4 and L4.4 mosquito cells

Cell homogenates from U4.4 and L4.4 mosquito cell clones were fractionated by multiple differential centrifugations. Three fractions of each cell line were designated: P15, light membranes, and cytosolic fractions and were compared to each other by two dimensional gel electrophoresis. A unique 55 kDa protein designated P55 was found in the P15 fraction of L4.4 cells (FIG. 1F) which was not labeled in the comparable fraction of U4.4 cells (FIG. 1E). P55 could not be detected in the light membrane or cytosolic fractions of either U4.4 or L4.4 cells (FIGS. 1A, 1B, 1C and 1D).

EXAMPLE 10
P55 is induced by the antiviral protein

The phenotypic differences between U4.4 cells and L4.4 cells are that L4.4 cells constitutively produce the antiviral protein and do not replicate Sindbis virus RNA. To illustrate the relationship between P55 synthesis and treatment with antiviral protein, [$^{35}$S] methionine/cysteine labeled U4.4 monolayers were treated with AVP for 24 or 48 hours and cell homogenates were fractionated. The P15 fraction produced from AVP-treated cells was subjected to two-dimensional gel electrophoresis. The P15 fraction from nontreated U4.4 cells served as A negative control and the P15 fraction from L4.4 cells served as a positive control.

Figure 2:
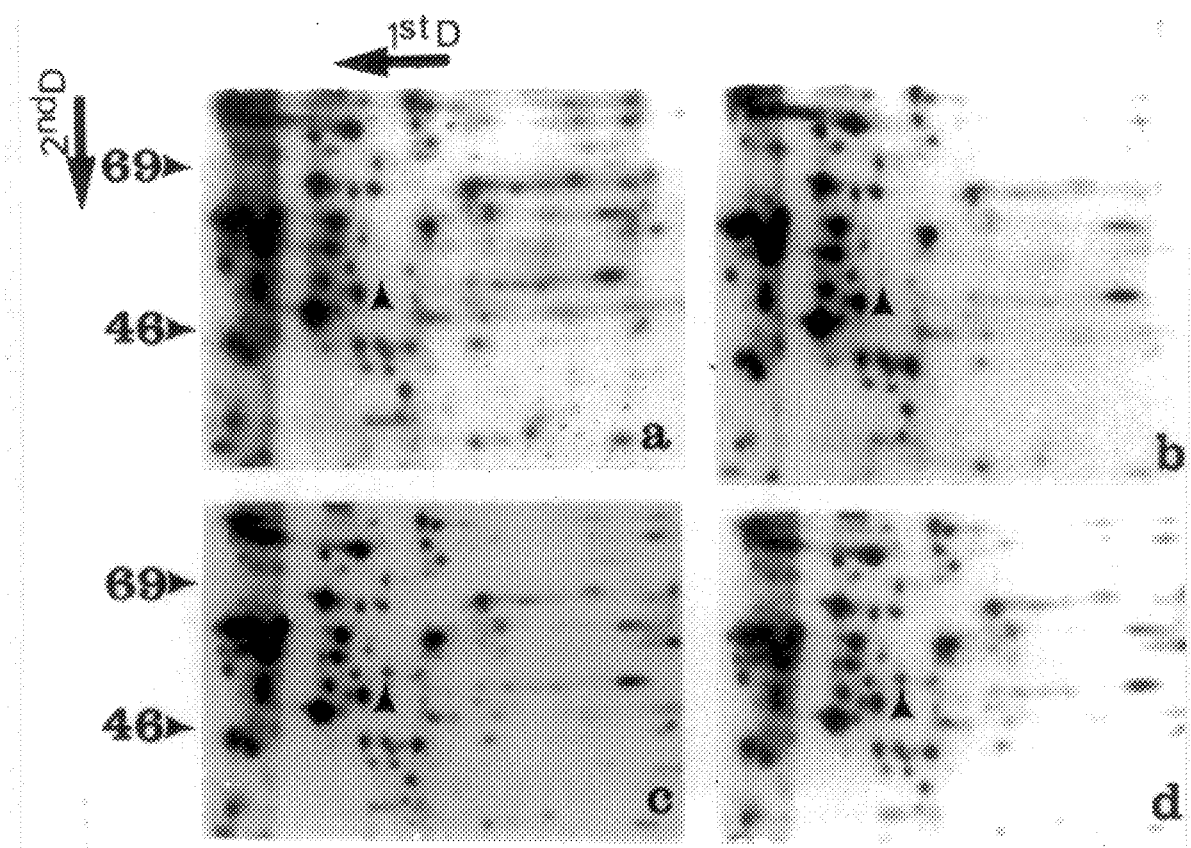
FIG. 2 shows the time course of induction of P55 by antiviral protein.

FIG. 2 demonstrates that after 48 hours of treatment of U4.4 cells with AVP, the amount of P55 reached about the same levels (FIG. 2C) as that in the L4.4 control (FIG. 2D). After 24 hours of treatment the amount of P55 detected was less than half the amount seen after 48 hours (FIG. 2B). Thus, AVP treatment induces synthesis of P55. This result coincides with the fact that the virus-resistant phenotype is completely established at 48 hours after AVP treatment of susceptible cells. Thus, the increase in P55 concentration in the cells corresponds to the reduction in the ability of the AVP-treated cells to replicate viral RNA and to produce progeny virus. P55 cannot be induced by AVP treatment of baby hamster kidney (BHK) cells or C7/10 mosquito cells. This is consistent with the fact that the antiviral phenotype cannot be established by treatment of BHK cells with AVP and that C7/10 cells neither produce nor respond to AVP.

EXAMPLE 11
Cellular localization of P55

Figure 3:
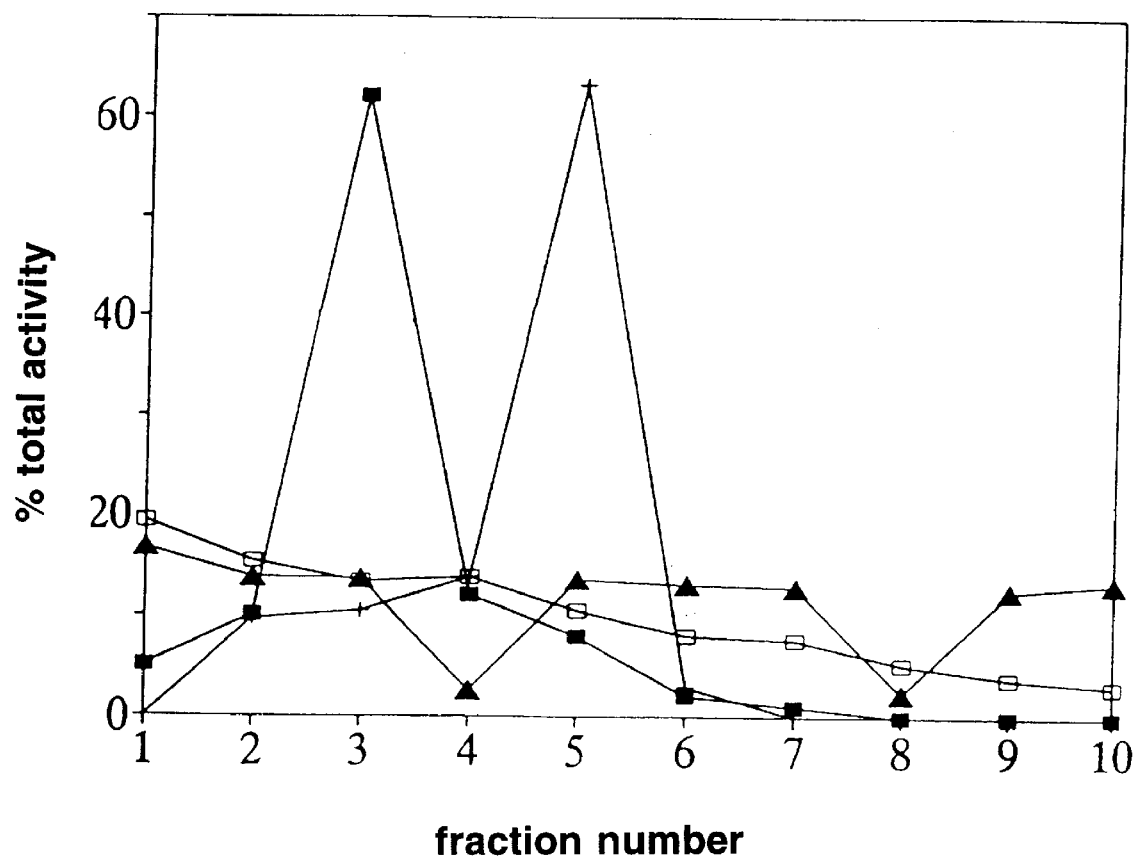
FIG. 3 shows the fractionation of P15 fraction of *Aedes albopictus* cells on continuous density gradients. Equal amounts of total cellular proteins (produced as in FIG. 1) were analyzed. The resuspended P15 fractions from U4.4 and L4.4 cells were centrifuged on Accudenz 20–40% gradients for 1 hour and 50 minutes at 52,000×g. Gradients were fractionated and the fractions were assayed for lysosomal (filled squares), mitochondrial (+), peroxisomal (*) and plasma membrane (filled triangles) marker enzyme activities.
Figure 4:
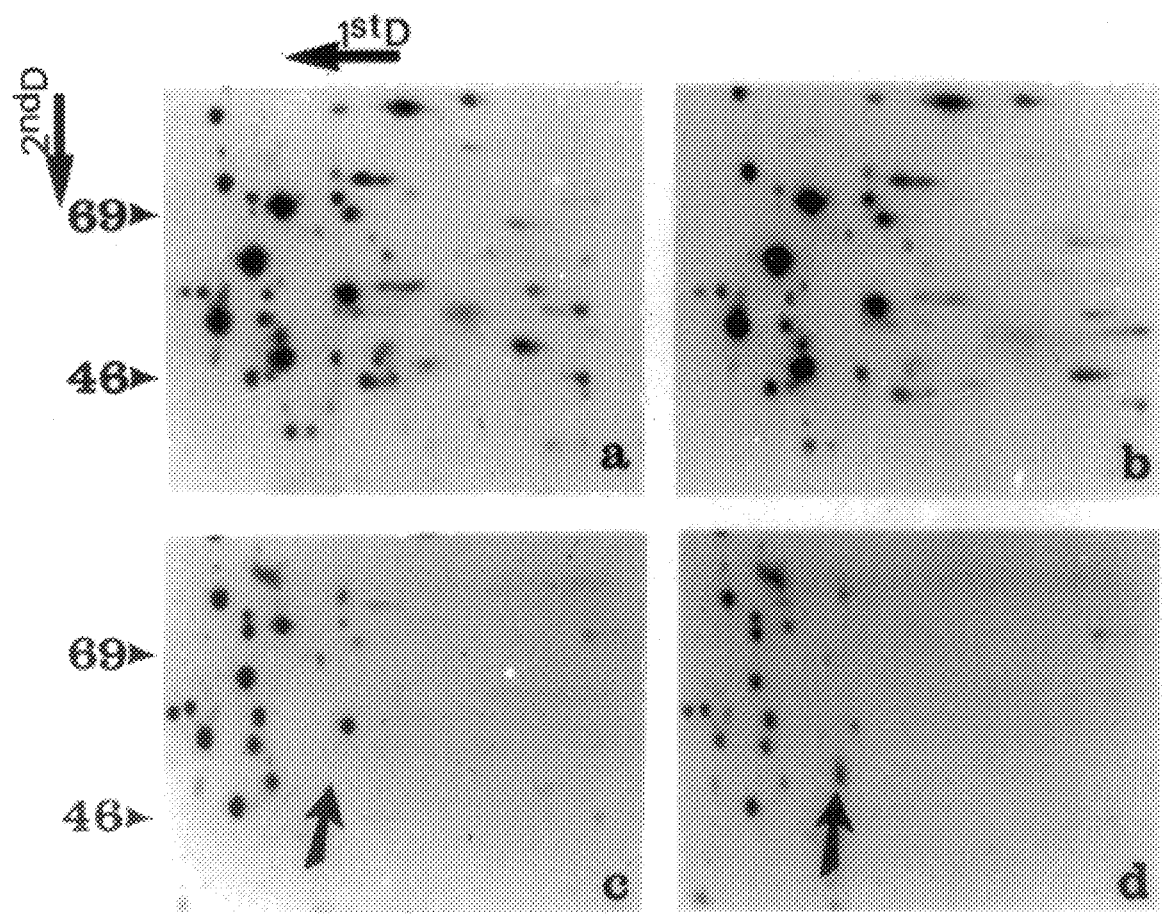
FIG. 4 shows the cellular location of P55. Fractions from the gradients shown in FIG. 4 corresponding to mitochondria and lysosomes were concentrated and analyzed by two dimensional gel electrophoresis.

P15 fractions from U4.4 and L4.4 cells were further analyzed by centrifugation through 20–40% continuous accudenz gradients. Two bands were observed, one at a density of 1.102 g/ml and the other at a density of 1.130 g/ml (FIG. 3). Each fraction of the resulting gradient was assayed for four marker enzyme activities [Beta-Galactosidase (lysosomes), Succinate INT reductase (mitochondria), Catalase (peroxisomes) and 5'-Nucleotidase (plasma membrane)] as described in Example 6. The enzyme assays revealed that the two bands observed in the gradient represented lysosomes (fraction No. 3) and mitochondria (fraction No. 5). Catalase and 5'-Nucleotidase enzyme assays showed that these two major bands were not significantly contaminated by other cellular organelles. The gradient fractions containing lysosomes and mitochondria were collected and diluted with gradient buffer and centrifuged for 10 minutes at 15,000×g to pellet the lysosomes or mitochondria. The pelleted lysosomes and mitochondria were subjected to 2-D gel electrophoresis. The protein P55 was associated with the lysosomes of L4.4 cells (FIG. 4D) but was absent in U4.4 cell lysosomes (FIG. 4C) and the mitochondria of both U4.4 and L4.4 cells (FIG. 4A and 4B).

The present invention shows that the virus-resistant L4.4 cells contain a 55 kDa lysosome-associated protein which is not detectable in virus-sensitive U4.4 cells. A direct relationship exists between treatment of virus-susceptible cells with AVP and the initiation of P55 production. P55 is present at concentrations equivalent to that found in L4.4 cells after a 48 hour AVP treatment of virus-susceptible U4.4 cells. P55 can be detected at lower concentrations after a 24 hour treatment with AVP. The relationship between P55 induction and acquisition of virus-resistance indicates that P55 is directly involved in the inhibition of viral RNA synthesis.

The Sindbis viral RNA replication complex consists of viral plus and/or minus strand RNA, viral nonstructural proteins, nsP1, 2, 3 and 4 and some host proteins. Barton et al. (1991) isolated an alphavirus replication complex from the P15 fraction of infected baby hamster kidney cells. Such a complex has not yet been identified in insect cells. In the present invention, the P15 fraction from mosquito cells was found to contain mitochondria and lysosomes and P55 was found specifically associated with lysosomes.

In mammalian cells the alphavirus replication complex is associated with the cytoplasmic surface of lysosomal membranes. If this is also the case in mosquito cells, the presence of P55 may alter the properties of the lysosomal membrane such that the alphaviral RNA and nonstructural proteins cannot develop the membrane associations required for replication.

The present invention also comprises a method of inhibiting the transmission of alphaviruses. Given the benefit of the present disclosure, such a method would be readily developed by one having ordinary skill in this art. For example, the gene encoding the protein P55 would be identified and cloned. Subsequently, the protein P55 would be expressed in mosquitoes by a method described by McGrane, et al., *Am. J. Trop. Med. Hyg.*, 39:502–510, 1988. Larvae which constitutively produce P55 protein are raised to adults. Adult mosquitoes are then resistant to infection by alphaviruses. Release of these insects into the wild will dilute the percentage of mosquitoes capable of carrying alphaviruses.

The present invention is also directed to a method of inhibiting viral, including alphaviral, RNA synthesis. The protein P55 is used to inhibit alphavirus RNA synthesis in cultured mammalian cells. Initially, insect cells which produce the protein P55 are fused with tissue-cultured mammalian cells. The cell hybrid is infected with alphavirus (Sindbis) and production of virus RNA is determined. Thereafter, mammalian cells are transfected with cloned P55 DNA to produce a mammalian cell line which produces the P55 protein. The P55 protein is then available for use as an antiviral agent.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated and purified protein that is produced by *Aedes albopictus* AVP-induced cells in vitro, wherein said protein has a molecular weight of 55 kDa as determined by SDS-PAGE, co-purifies with membranes of lysosomes of said cells, and induces a non-transient virus resistant state in said *Aedes albopictus* cells to infection by Sindbis virus.

2. A pharmaceutical composition, comprising the protein of claim 1 and a pharmaceutically acceptable carrier.

3. A method of preparing the protein of claim 1, comprising the steps of:

culturing *Aedes albopictus* L4.4 cells, ATCC No. CRL 11699 in a medium at a temperature of about 28° C.;

harvesting the cells and disrupting the cellular membrane of said cells; and isolating and purifying said protein from said cells.

* * * * *

UNITED STATES PATENT AND TRADEMARK OFFICE
CERTIFICATE OF CORRECTION

PATENT NO. : 5,817,619
DATED : October 6, 1998
INVENTOR(S) : Dennis T. Brown

Page 1 of 1

It is certified that error appears in the above-identified patent and that said Letters Patent is hereby corrected as shown below:

Coumn 1,
Line 2, "METHOD" should read -- METHODS --.

Column 4,
Line 27, "Aedes" should read -- *Aedes* --.
Line 28, "albopictus" should read -- *albopictus* --.
Line 45, "*Viroloay*" should read -- *Virology* --.

Column 6,
Line 26, please start a new paragraph beginning with the word "5'-Nucleotidase".
Line 27, please replace the period after the word "AMP" with a comma.
Line 47, please insert a comma after the word "*Cell*12" and delete the period.
Line 49, "In" should read -- *In* --.
Line 52, please insert a comma after the word "urea" and delete the period.
Line 53, please insert a comma after the word "bisacrylamide" and delete the period.

Signed and Sealed this

Twenty-second Day of January, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 5,817,619
DATED : October 6, 1998
INVENTOR(S) : Dennis T. Brown

It is certified that error appears in the above-identified patent and that said Letters Patent is hereby corrected as shown below:

Column 1,
Lines 2-3, please insert -- The United States government may own certain rights to this invention pursuant to grant number AI 14710 from the National Institutes of Health. --.

Signed and Sealed this

Twenty-fifth Day of October, 2005

JON W. DUDAS
*Director of the United States Patent and Trademark Office*